(12) United States Patent
Connor et al.

(10) Patent No.: US 9,804,216 B2
(45) Date of Patent: Oct. 31, 2017

(54) DETECTION OF ELECTROMAGNETIC FIELD WITH ELECTROACTIVE POLYMERS

(71) Applicant: International Business Machines Corporation, Armonk, NY (US)

(72) Inventors: Samuel R. Connor, Apex, NC (US); Michael A. Cracraft, Poughkeepsie, NY (US); Jonathan W. Jackson, Durham, NC (US); Joseph Kuczynski, North Port, FL (US)

(73) Assignee: International Business Machines Corporation, Armonk, NY (US)

(*) Notice: Subject to any disclaimer, the term of this patent is extended or adjusted under 35 U.S.C. 154(b) by 37 days.

(21) Appl. No.: 15/071,314

(22) Filed: Mar. 16, 2016

(65) Prior Publication Data

US 2017/0269144 A1    Sep. 21, 2017

(51) Int. Cl.
*G01R 29/12* (2006.01)
*G01R 31/14* (2006.01)
*G01R 15/16* (2006.01)
*G01N 27/60* (2006.01)
*G01R 5/28* (2006.01)

(52) U.S. Cl.
CPC ........... *G01R 29/12* (2013.01); *G01R 15/165* (2013.01); *G01R 31/14* (2013.01); *G01N 27/60* (2013.01); *G01R 5/28* (2013.01)

(58) Field of Classification Search
CPC ........ G01R 29/12; G01R 15/165; G01R 3/14; G01R 5/28; G01N 27/60
USPC .................................................. 324/457, 458
See application file for complete search history.

(56) References Cited

U.S. PATENT DOCUMENTS

| 5,359,319 | A | * | 10/1994 | Campbell | ............. G01R 29/12 324/457 |
| 5,673,028 | A | | 9/1997 | Levy | |
| 6,014,305 | A | | 1/2000 | Yu | |
| 6,583,612 | B2 | | 6/2003 | Karins et al. | |
| 7,151,655 | B2 | | 12/2006 | Choo | |
| 2005/0258842 | A1 | | 11/2005 | Maloney | |
| 2011/0025339 | A1 | | 2/2011 | Wallash | |
| 2013/0207793 | A1 | * | 8/2013 | Weaber | ............. G06F 1/1601 340/407.2 |
| 2014/0184253 | A1 | | 7/2014 | Nelsen et al. | |
| 2015/0355253 | A1 | | 12/2015 | Ayotte et al. | |

FOREIGN PATENT DOCUMENTS

WO         2007101448         9/2007

* cited by examiner

*Primary Examiner* — Amy He
(74) *Attorney, Agent, or Firm* — Lieberman & Brandsdorfer, LLC

(57) ABSTRACT

Embodiments relate to a method, apparatus, and system for passively detecting strength of an electromagnetic field. An electroactive polymer (EAP) is configured with an antenna in communication with an RC circuit. The EAP is positioned proximal to a sensor. In response to receipt of a transient electromagnetic pulse due to an electrostatic discharge, the circuit captures the received pulse and transmits the pulse to the EAP. The EAP reacts to the pulse in the form of a deflection. The magnitude of the deflection correlates to the field strength which caused the received pulse. As deflection of the EAP is communicated to the proximally positioned sensor, a recording of the electrostatic discharge takes place.

16 Claims, 7 Drawing Sheets

DETECTION OF ELECTROMAGNETIC FIELD WITH ELECTROACTIVE POLYMERS

BACKGROUND

The present invention relates to detection of electromagnetic field strength. More specifically, the invention relates to a method and product for sensing an electrostatic discharge.

Electrostatic discharge (ESD) is the sudden flow of electricity between two objects with different electric potentials whereby the two objects are brought so close together that the dielectric between them breaks down. In essence, ESD is static electricity flow between the two objects, and as a characteristic of such a current, electromagnetic fields (EMFs) are created therefrom. The ESD event can damage a device, which in some circumstances may continue to function, thereby causing a latent defect.

Semiconductor devices are particularly sensitive to ESD. Detecting exposure of semiconductor components to ESDs, and their resulting EMFs, is critical to determining whether the components have been taken outside their operating envelope. The art of detecting EMFs has developed over time to include the use of a variety of equipment and methods including the use of electrochromic materials, balun transformers, magneto-optic devices, oscilloscopes, and magnetometers.

SUMMARY

This invention comprises a method, apparatus, and system for detecting a threshold strength of an electromagnetic field.

In one aspect, a method is provided to detect electromagnetic field strength. An electroactive polymer (EAP) is configured to have electrical communication with at least one antenna. The EAP captures a transient electromagnetic pulse from an electrostatic discharge. More specifically, the circuit captures the received pulse, stores it, and communicates the stored pulse to the EAP. In response to the received communication, the EAP is subject to a movement in the form of a deflection in correlation to the field strength of the received pulse. This movement response by the EAP can then be measured to correlate with the strength of the received pulse.

In another aspect, an electromagnetic field detection device is provided. An antenna is provided and in electrical communication with a resistor-capacitor (RC) circuit and an EAP, such that an EMF signal may be received by the antenna, stored, and communicated to the EAP. A sensor is provided and positioned such that a threshold magnitude of the signal will produce a deflection of the EAP, resulting in the sensor being engaged. Embodiments may include multiple sensors positioned at varying distances from the EAP for recordation of multiple magnitude levels.

In yet another aspect, an EMF detection system is provided. An antenna is provided in electrical communication with an RC circuit. Similarly, an EAP is provided in communication with the circuit. A sensor is provided and positioned in such a way that a certain magnitude of deflection by the EAP may engage the sensor and record the event. The components are within, or in the vicinity of, an EMF. The components of the system are related such that if the EMF strength is below a certain threshold, resulting deflections of the EAP do not engage the sensor; however, EMF strength at or above a certain threshold will cause a deflection of the EAP sufficient to engage the sensor and record the event.

These and other features and advantages will become apparent from the following detailed description of the presently preferred embodiment(s), taken in conjunction with the accompanying drawings.

BRIEF DESCRIPTION OF THE SEVERAL VIEWS OF THE DRAWINGS

The drawings referenced herein form a part of the specification. Features shown in the drawings are meant as illustrative of only some embodiments, and not of all embodiments unless otherwise explicitly indicated.

DETAILED DESCRIPTION

It will be readily understood that the components of the present invention, as generally described and illustrated in the Figures herein, may be arranged and designed in a wide variety of different configurations. Thus, the following detailed description of the embodiments of the apparatus, system, and method of the present invention, as presented in the Figures, is not intended to limit the scope of the invention, as claimed, but is merely representative of selected embodiments of the invention.

Reference throughout this specification to "a select embodiment," "one embodiment," or "an embodiment" means that a particular feature, structure, or characteristic described in connection with the embodiment is included in at least one embodiment of the present invention. Thus, appearances of the phrases "a select embodiment," "in one embodiment," or "in an embodiment" in various places throughout this specification are not necessarily referring to the same embodiment.

The illustrated embodiments of the invention will be best understood by reference to the drawings, wherein like parts are designated by like numerals throughout. The following description is intended only by way of example, and simply illustrates certain selected embodiments of devices, systems, and processes that are consistent with the invention as claimed herein.

An RC circuit, as disclosed with respect to the embodiment(s), refers to a resistor-capacitor (RC) circuit. The simplest form of an RC circuit comprises one resistor and one capacitor. The RC circuit may comprise more than one capacitor and more than one resistor in a variety of circuit arrangements. Voltage applied to an RC circuit is stored in the capacitor and is discharged over time through the resistor. The arrangement of an RC circuit allows for a temporary storage of voltage potential, which decreases over time as a function of the resistance, capacitance, and voltage across the capacitor. Utilizing an RC circuit enables sharp and sudden pulses to be captured and their affect stored for a period of time long enough to allow a slower reacting component, such as an electroactive polymer (EAP) material, to react to the electrical stimuli.

A rectifier circuit, as disclosed with respect to the embodiments, refers to a circuit which rectifies current to a single direction. By using a configuration of diodes or their functional equivalent, the rectifier circuit outputs voltage in the same polarity regardless of the voltage polarity of the input current. Rectifier circuits may be utilized to rectify pulses of varying polarities into a single polarity or transmit pulses of only a chosen polarity.

Figure 1:
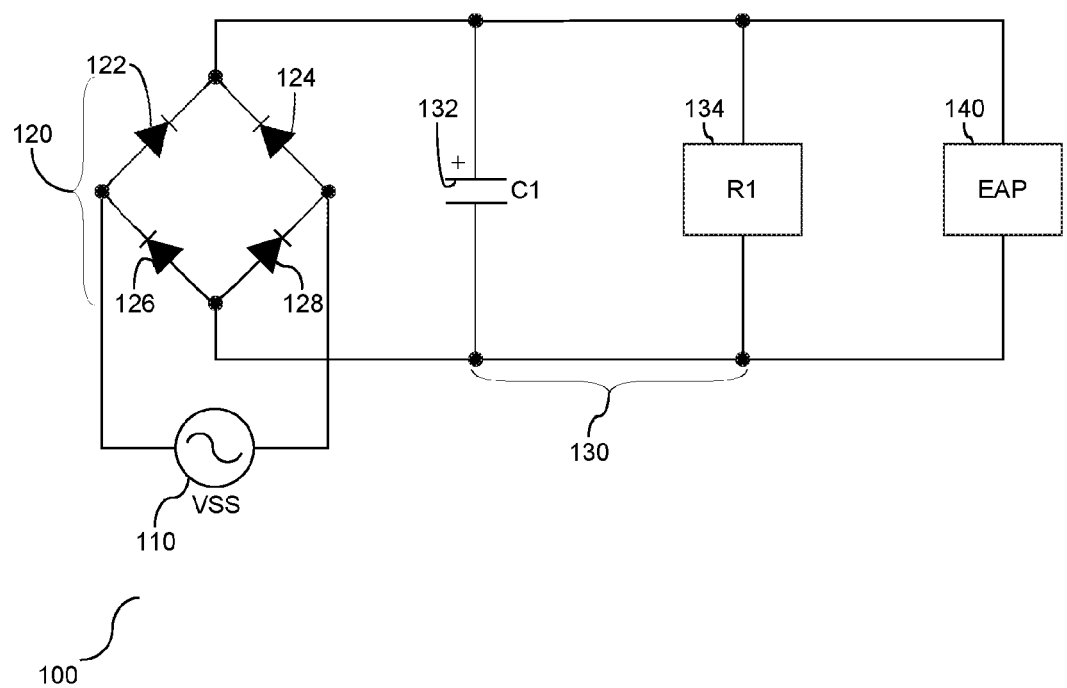
FIG. 1 depicts a circuit diagram in accordance with an embodiment of the invention.

With reference to FIG. 1, a circuit diagram of an electrostatic sensing device (100) is provided. An antenna (represented by the circuit element generating the pulses (110)) is provided, wherein the antenna is capable of receiving pulses (110) generated by EMFs that originate from ESDs. The pulses (110) are communicated to a rectifying circuit (120) which rectifies the pulses (110) to a polarized pulse. In one embodiment of the invention, as is shown in FIG. 1, the rectifying circuit comprises diodes (122), (124), (126), and (128), arranged in a manner that rectifies the polarity of the pulse (110) received into a polarized pulse. It is anticipated that the rectifying circuit can include a variety of circuit arrangements and number of diodes. The polarized pulses are then communicated to an RC circuit (130) which stores the pulse energy. Although FIG. 1 illustrates the RC circuit (130) to be composed of a capacitor (132) and a resistor (134), it is anticipated that the RC circuit may take other embodiments that yield the effect of storing energy. The polarized pulse is then communicated to the EAP (140), which responds by deflecting, or changing shape, due to the electrical stimulation. In general, a stronger magnitude pulse (110) communicated to the EAP (140) yields a larger deflection by the EAP (140).

Figure 2:
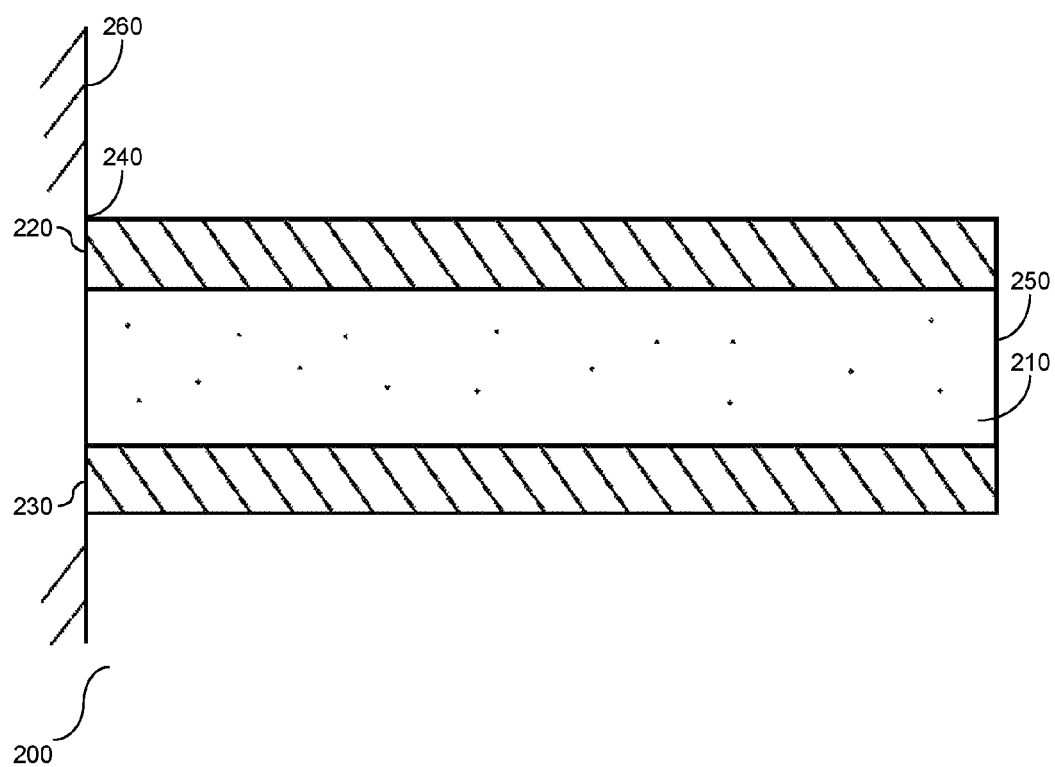
FIG. 2 depicts a cross-sectional view of a non-stimulated electroactive polymer.

Referring to FIG. 2, a cross sectional view of non-stimulated electroactive polymer (EAP) (200) is shown. The EAP comprises a dielectric polymer material (210) configured to react to electrical fields with physical movement. In order to create the electrical field that stimulates the polymer to react, the polymer is shown herein inserted and affixed in between conductive surfaces (220) and (230), which are each in electrical communication with the circuit of the electrostatic sensing device (100). As shown in FIG. 2, the EAP (200) has a proximal end (240), which is affixed to a secondary object (260), and a distal end (250). Furthermore, the EAP (200) is shown herein in an unstimulated state, also referred to herein as a neutral state, due to the lack of voltage potential between conductive surfaces (220) and (230).

Figure 3:
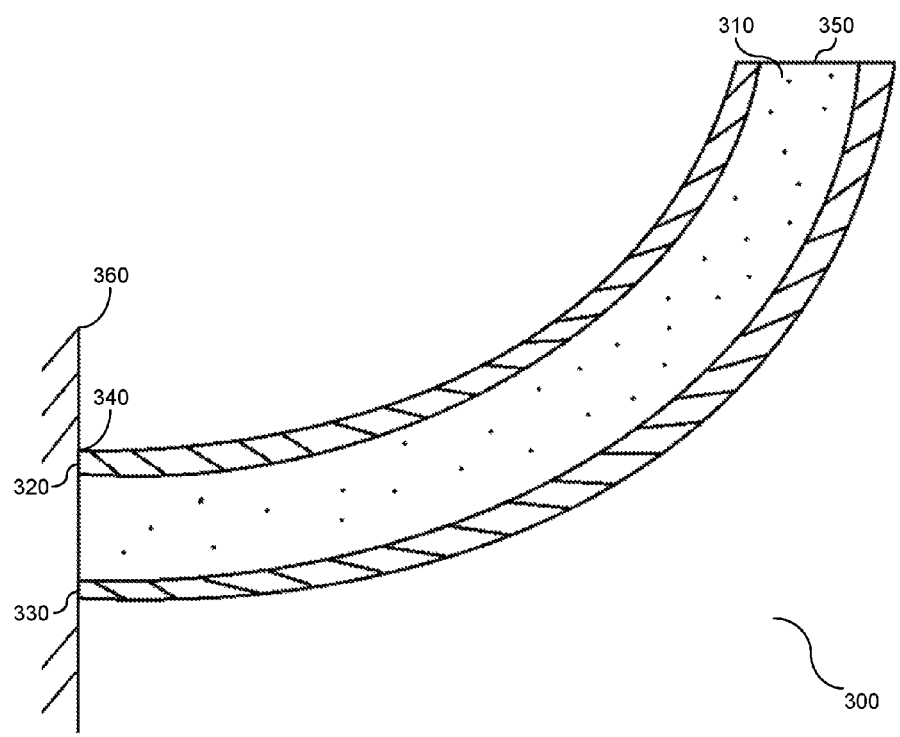
FIG. 3 depicts a cross-sectional view of a stimulated electroactive polymer.

With reference to FIG. 3, a cross sectional view of an EAP (300) in a stimulated state, also referred to herein as a second state or non-neutral state, is shown. More specifically, the depicted EAP (300) is shown with a proximal end (340) and a distal end (350). The proximal end (340) is represented as fixed to a secondary object (360) while the distal end (350) is shown non-fixed to any secondary surface or object. The dielectric polymer material (310) is shown with two opposing and conductive surfaces (320) and (330). In the stimulated state, a voltage differential between the conductive surfaces (320) and (330) is present, and this differential causes the dielectric polymer material (310) to deflect from its neutral state shown in FIG. 2 to the stimulated state shown herein. In one embodiment, the EAP may deflect in a different direction than that shown herein. The deflection of the EAP is merely an example of a form and direction of deflection. By way of example, the stimulated state represents a curve of the EAP (300) in a direction. In one embodiment, the direction with which the EAP curves is determined by the polarity of the voltage differential between the conductive surfaces (320) and (330). Accordingly, a pulse (110) that has been rectified to a polarized pulse will cause the EAP (140) to deflect in a direction dictated by the configured polarization of the rectifier circuit (120).

Figure 5A:
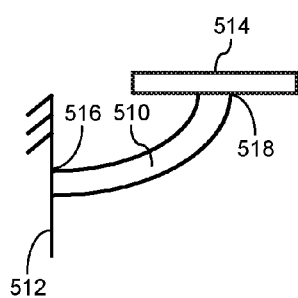
FIGS. 5A, 5B, 5C, and 5D depict various interactions between an electroactive polymer and a sensor in accordance with embodiments of the invention.

The deflection of the EAP (140) can be measured visually or used to engage a sensor which thereby records the event of the deflection. Embodiments are envisioned whereby sensors are proximally placed in a single direction of deflection. Referring to FIG. 5A, a diagram is provided illustrating a stimulated EAP (510) fixed to an object (512) by the proximal end (516) and engaging a sensor (514) position adjacent to the distal end (518). Actuation of the sensor (514) records the event of the deflection upon being engaged by the EAP (510). FIG. 5B depicts another example embodiment where an EAP (540), which is fixed at both the proximal end (548) and distal end (550) to a first secondary object (542) and second secondary object (544), respectively. The EAP (540) is shown herein stimulated by a pulse and deflected in one direction towards a sensor (546), which records the event of the deflection upon being engaged by the EAP (540). Although FIGS. 5A and 5B depict one sensor proximally located in one direction of deflection with respect to the EAP, multiple passive sensors are contemplated as well, whereby each passive sensor records a different threshold of deflection magnitude by the EAP.

Figure 4:
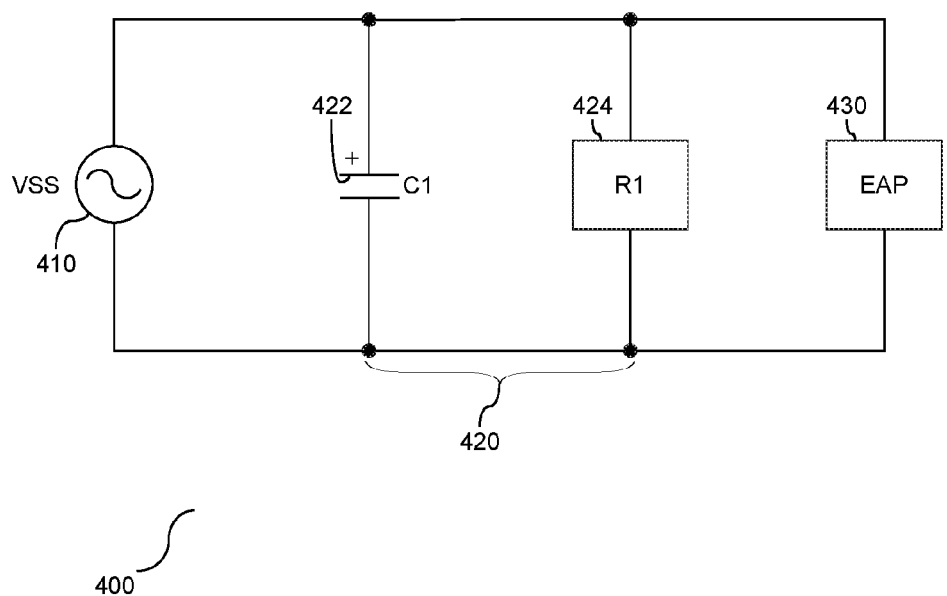
FIG. 4 depicts a circuit diagram in accordance with an embodiment of the invention.

Referring to FIG. 4, a circuit diagram of an alternative embodiment of an electrostatic sensing device (400) is provided. In comparison to the circuit shown and described in FIG. 1, the circuit diagram (400) does not include a rectifying circuit. An antenna (represented by the element generating the pulses (410)) is provided in direct communication with the RC circuit (420). In absence of a rectifier circuit, the antenna is able to communicate pulses (410) of opposite polarities to the RC circuit (420). The RC circuit in the depicted embodiment has a capacitor (422) and resistor (424), but other varieties of circuit arrangements with the effect of storing energy may also be used. The pulses (410) are stored in the RC circuit (420) and communicated to the EAP (430). In response to pulses (410) of differing polarities, the EAP (430) will deflect in different directions, depending on the polarity of the pulse (410) received. Because the EAP (430) may deflect in different directions, sensors may be placed proximal to any of these deflection areas.

Figure 5C:
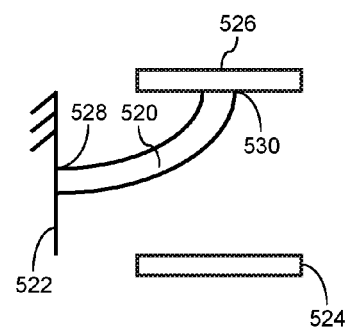
Figure 5B:
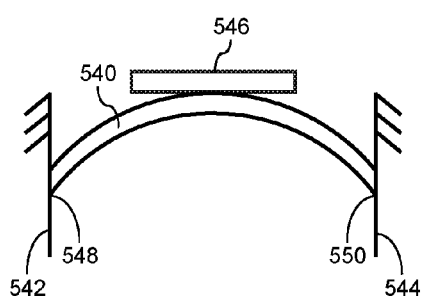

Referring to FIG. 5C, a diagram is provided illustrating a stimulated EAP in communication with the circuit shown in FIG. 4. An EAP (520) is shown in electrical communication to a non-polarized electrostatic sensing device (400). More specifically, the EAP (520) is shown fixed at a proximal end (528) to a secondary object (522). The distal end (530) is shown positioned adjacent to sensors (524) and (526). In the example shown herein, the EAP (520) is shown with the distal end (530) deflected and engaging sensor (526). Upon stimulation by a pulse (410) of an opposite polarity, the EAP (520) will deflect towards sensor (524).

Figure 5D:
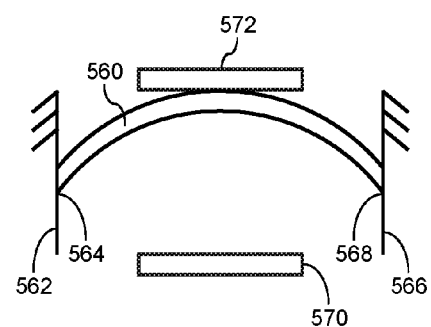

With reference to FIG. 5D, a diagram is provided illustrating a stimulated EAP in communication with the non-polarized electrostatic sensing device (400). More specifically, the EAP (560) is shown be fixed at a proximal end (564) and distal end (568) to secondary objects (562) and (566), respectively. Sensors (570) and (572) are shown positioned proximal to the EAP (560). In one embodiment, and as shown herein, the EAP (560) has been stimulated and engages sensor (572). Upon stimulation by a pulse (410) of an opposite polarity, the EAP (560) will deflect towards sensor (570). In one embodiment, multiple passive sensors may be positioned proximal to the EAP (560), whereby each passive sensor records a different threshold of deflection magnitude by the EAP.

Figure 6:
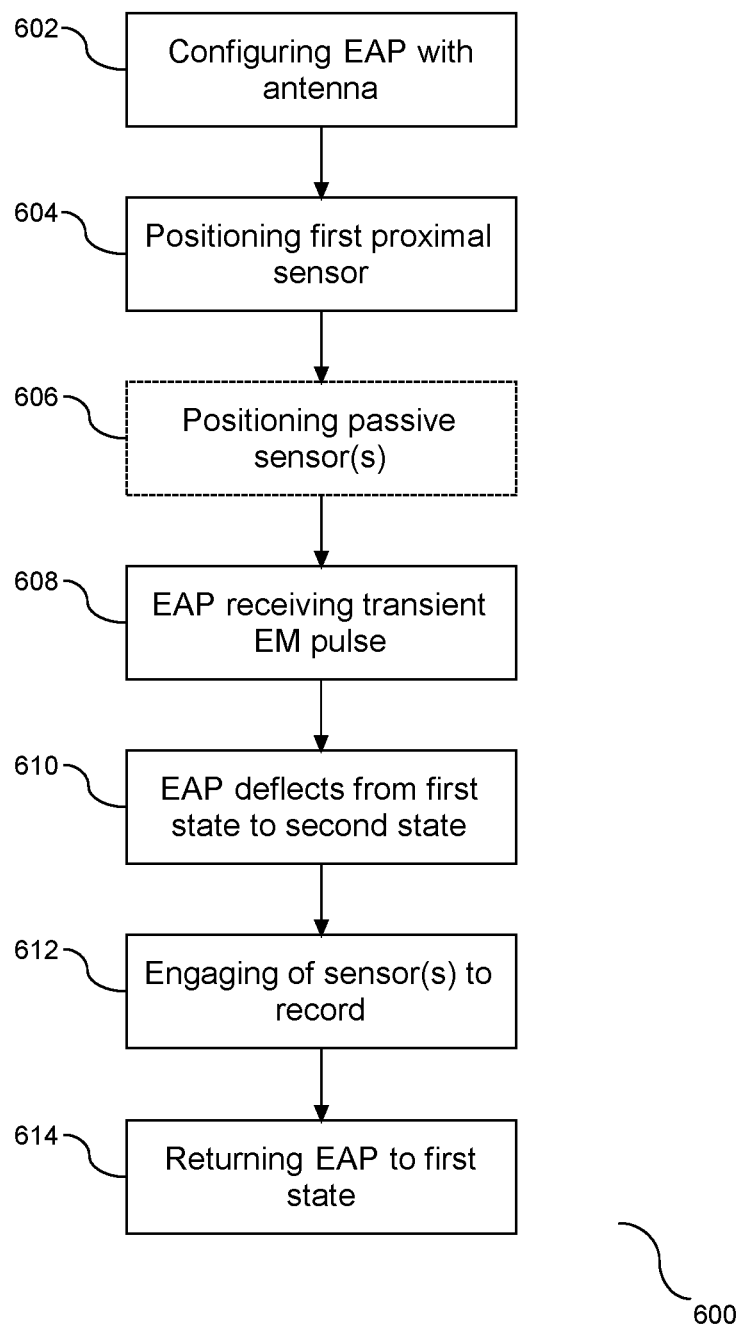
FIG. 6 depicts a flowchart for configuring an electrostatic sensing device for detecting and communicating receipt of an electromagnetic pulse.

As shown in FIGS. 1-5, an EAP is shown in communication with a circuit and positioned proximal to a sensor for communicating and an associated circuit are provided for detecting and communicating receipt of an electromagnetic pulse. Referring to FIG. 6, a method (600) of configuring an electrostatic sensing device is provided. As shown, an EAP is configured with at least one antenna in electrical communication with a circuit (602). In one embodiment, a rectifier circuit and/or an RC circuit is configured in electrical communication between the EAP and the antenna at step (602). A first sensor is positioned proximal to the EAP (604). In one embodiment, a threshold deflection of the EAP may engage the sensor therefore recording an ESD event. Optionally, one or more passive sensors may be positioned relative to the EAP (606) in order to record varying levels of magnitude of the EAP deflection. Accordingly, prior to recording activity, the EAP is configured to receive and record an ESD event.

As shown herein, following configuration, the EAP receives a transient electromagnetic pulse (608) which has been captured by the antenna and transmitted through the electrostatic sensing device circuit. In reaction to the transient electromagnetic pulse, the EAP deflects from a first state to a second state (610). In the deflection to the second state at step (610), the EAP engages the first sensor and/or one or more passive sensors (612), with the engaged sensor(s) recording the ESD event. After the ESD event occurs and has been recorded, the EAP returns to its first state (614), e.g. non-deflected state.

Figure 7:
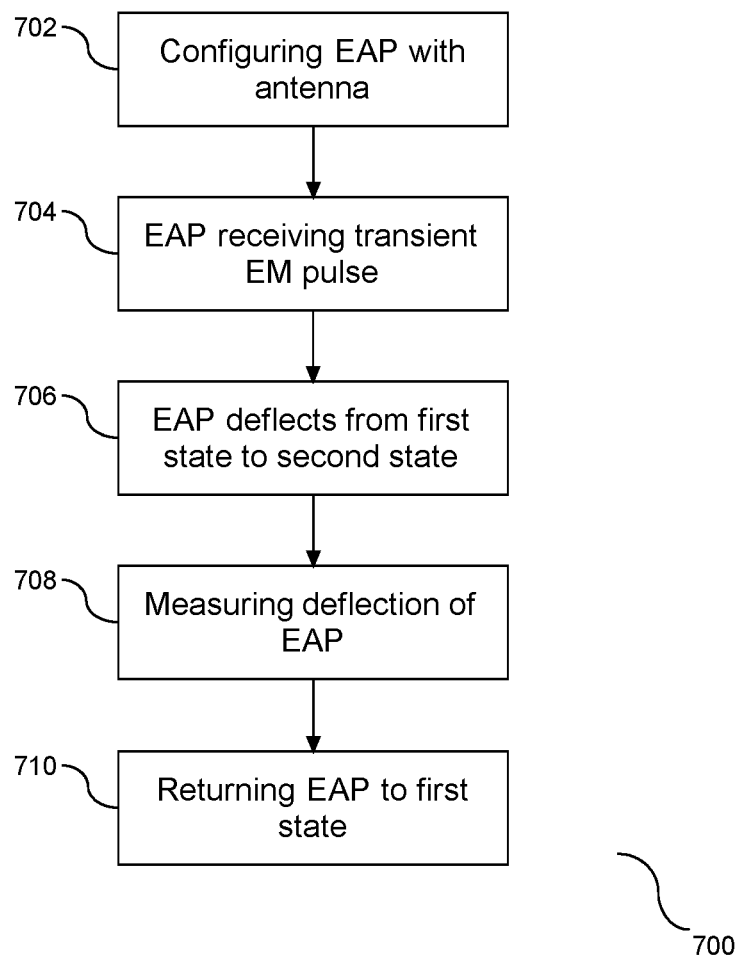
FIG. 7 depicts a flow chart for configuring an electrostatic sensing device for detecting and measuring an electromagnetic pulse.

Referring to FIG. 7, a flow chart (700) is provided illustrating a process for detecting and communicating receipt of an electromagnetic pulse. Similar to the process shown in FIG. 6, the EAP is configured (702) with at least one antenna in electrical communication with the EAP. The configuration (702) may further include a rectifier circuit and/or an RC circuit in communication with the antenna and EAP. Following configuration, the EAP is shown in receipt of a transient electromagnetic pulse (704) which has been captured by the antenna and transmitted through the electrostatic sensing device circuit. In reaction to the transient electromagnetic pulse, the EAP deflects from a first state to a second state (706). The deflection of the EAP is observed and measured (708), whereby the measurement of the deflection corresponds to the severity of the ESD event. After the ESD event occurs and has been measured, the EAP returns to its first state (710), e.g. non-deflected state.

The flowchart and block diagrams in the Figures illustrate the architecture, functionality, and operation of possible implementations of systems, methods, and computer program products according to various embodiments of the present invention. In this regard, each block in the flowchart or block diagrams may represent a module, segment, or portion of instructions, which comprises one or more executable instructions for implementing the specified logical function(s). In some alternative implementations, the functions noted in the block may occur out of the order noted in the figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

Embodiments may include multiple passive sensors wherein the sensors are positioned relative to the EAP in order to record deflections of the EAP at different magnitudes. Different deflection magnitudes correlate with different EMF strengths. Accordingly, the sensors may be positioned and configured relative to the EAP to effectively gauge the strength of an ESD event.

Similarly, embodiments may also include multiple antennae wherein the antennae are placed in different locations to capture pulses from different areas or capture pulses of different polarities, spectrums, etc. The multiple antennae can be in communication with a common circuit or in communication with multiple circuits.

Embodiments may also include the use of multiple EAPs, in communication with the same circuit or in communication with multiple circuits. The EAPs may be of differing thicknesses, differing polymer chemical structure, and/or differing electroactive properties such that the deflection of each EAP differs when stimulated with a given pulse strength. Such an arrangement may allow for the recordation of pulses of differing magnitude by determining which EAP material deflected with sufficient magnitude to engage their corresponding sensor(s).

Other contemplated embodiments include affixing a writing instrument onto the deflecting end of an EAP and installing the EAP onto a dynamic recording device, such as a spinning recorder or chart recorder. By doing so, deflections of the EAP may be translated into visually observable marks made by the writing instrument onto a surface of the dynamic recording device. This embodiment would allow for the recordation of not only the magnitude of the deflections, but the relative time of when they occurred and how many events occurred within a period of time.

The terminology used herein is for the purpose of describing particular embodiments only and is not intended to be limiting of the invention. As used herein, the singular forms "a", "an" and "the" are intended to include the plural forms as well, unless the context clearly indicates otherwise. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof.

The corresponding structures, materials, acts, and equivalents of all means or step plus function elements in the claims below are intended to include any structure, material, or act for performing the function in combination with other claimed elements as specifically claimed. The description of the present invention has been presented for purposes of illustration and description, but is not intended to be exhaustive or limited to the invention in the form disclosed.

Many modifications and variations will be apparent to those of ordinary skill in the art without departing from the scope and spirit of the embodiments. The embodiments have been chosen and described in order to best explain the principles and the practical application of electrostatic sensing, and to enable others of ordinary skill in the art to understand the invention for various embodiments with various modifications as are suited to the particular use contemplated.

Alternative Embodiment

It will be appreciated that, although specific embodiments have been described herein for purposes of illustration, various modifications may be made without departing from the spirit and scope of the embodiments. Accordingly, the scope of protection is limited only by the following claims and their equivalents.

We claim:

1. A method comprising:
   creating an electrostatic sensing circuit, wherein creating the circuit comprises:
      providing an electroactive polymer (EAP); and
      configuring the EAP in electrical communication with at least one antenna;
   capturing an electromagnetic pulse from a discharge and communicating the electromagnetic pulse to the EAP;
   deflecting a state of the EAP from a first state to a deflected state in response to receipt of the communication; and
   measuring the deflected state of the EAP, wherein the measured deflection correlates with field strength of the received pulse.

2. The method of claim 1, wherein creating the electrostatic sensing circuit further comprises configuring an RC circuit in electrical communication between the antenna and the EAP.

3. The method of claim 2, wherein creating the electrostatic sensing circuit further comprises configuring a rectifier circuit in electrical communication between the antenna and the RC circuit.

4. The method of claim 2, further comprising affixing the EAP to a writing implement, wherein the writing implement is installed in communication with a dynamic recording device, the deflection of the EAP actuating the writing implement with respect to the dynamic recording device and the dynamic recording device registering indicia from the writing implement.

5. The method of claim 4, further comprising the dynamic recording device recording a quantity and time of the EAP deflection.

6. The method of claim 1, further comprising positioning a first sensor proximal to the EAP, wherein the measured deflection in excess of a threshold engages the first sensor, and recording the measured deflection of the EAP to the deflected state.

7. The method of claim 1, further comprising positioning two or more sensors proximal to the EAP, and further comprising multiple magnitudes of deflection of the EAP engaging a selection of the positioned sensors, with each magnitude of deflection corresponding to an electromagnetic pulse strength.

8. The method of claim 1, further comprising returning the EAP to the first state following engagement of one of the sensors.

9. An electromagnetic field detection device, the device comprising:
   an antenna;
   an RC circuit in electrical communication with the antenna, the RC circuit to store a signal received from the antenna;
   an electroactive polymer (EAP) in electrical communication with the RC circuit whereby the stored signal causes a deflection of the EAP; and
   a first sensor positioned proximal to the EAP, the first sensor having a first calibration, and a first threshold magnitude of deflection of the EAP to engage the first sensor.

10. The device of claim 9, further comprising a secondary sensor having a secondary calibration different from the first calibration, the secondary sensor positioned proximal to the EAP, and a second magnitude of deflection of the EAP to engage the second sensor.

11. The electromagnetic field detection device of claim 9, further comprising a rectifier circuit in electrical communication with the antenna and the EAP.

12. An electromagnetic field detection system, the system comprising:
   an antenna;
   an RC circuit in electrical communication with the antenna;
   an electroactive polymer (EAP) in electrical communication with the RC circuit;
   a sensor, positioned to engage upon a threshold deflection of the EAP; and
   an electromagnetic field causing a voltage potential in the EAP and a deflection of the EAP.

13. The system of claim 12, wherein the deflection of the EAP is not sufficient to engage the sensor.

14. The system of claim 12, further comprising the deflection of the EAP to engage the sensor, and the engagement to indicate a receipt of a threshold electromagnetic field strength in excess of a threshold.

15. The system of claim 12, further comprising one or more passive sensors positioned to record multiple magnitudes of deflection.

16. The system of claim 15, wherein the voltage potential in the EAP from the electromagnetic field causes the deflection of the EAP to engage the one or more passive sensors.

* * * * *